(12) United States Patent
Dochnahl et al.

(10) Patent No.: US 8,642,780 B2
(45) Date of Patent: Feb. 4, 2014

(54) N-CARBOMETHOXY-N-METHOXY-(2-CHLOROMETHYL)-ANILINES, THEIR PREPARATION AND THEIR USE AS PRECURSORS FOR PREPARING 2-(PYRAZOL-3'-YLOXYMETHYLENE)-ANILIDES

(75) Inventors: Maximilian Dochnahl, Mannheim (DE); Bernd Mueller, Frankenthal (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/583,787

(22) PCT Filed: Mar. 17, 2011

(86) PCT No.: PCT/EP2011/054020
§ 371 (c)(1),
(2), (4) Date: Sep. 10, 2012

(87) PCT Pub. No.: WO2011/113884
PCT Pub. Date: Sep. 22, 2011

(65) Prior Publication Data
US 2013/0005986 A1    Jan. 3, 2013

Related U.S. Application Data

(60) Provisional application No. 61/315,061, filed on Mar. 18, 2010.

(30) Foreign Application Priority Data

Mar. 18, 2010    (EP) ..................... 10156946

(51) Int. Cl.
*C07D 231/10* (2006.01)
*C07C 269/04* (2006.01)

(52) U.S. Cl.
USPC ........................ 548/371.1; 548/578; 560/29

(58) Field of Classification Search
USPC .................. 548/371.1, 578; 560/29
See application file for complete search history.

(56) References Cited

U.S. PATENT DOCUMENTS

| 5,824,705 A | 10/1998 | Mueller et al. |
| 5,869,517 A | 2/1999 | Mueller et al. |
| 6,252,083 B1 | 6/2001 | Mueller et al. |

FOREIGN PATENT DOCUMENTS

| EP | 1 845 086 | 10/2007 |
| JP | 07278090 | 10/1995 |
| WO | WO 93/15046 | 8/1993 |
| WO | WO 96/01256 | 1/1996 |

OTHER PUBLICATIONS

Database Registry Chemical Abstracts Service, Columbus, Ohio, Accession No. RN 173904-05-7, RN 173904-06-8, Entered STN: Mar. 6, 1996.*
International Preliminary Report on Patentability dated Sep. 18, 2012, from corresponding International Application No. PCT/EP2011/054020, filed Mar. 17, 2011.
International Search Report completed Apr. 13, 2011, in International Application No. PCT/EP2011/054020, filed Mar. 17, 2011.

* cited by examiner

*Primary Examiner* — Samantha Shterengarts
(74) *Attorney, Agent, or Firm* — Brinks Gilson & Lione

(57) ABSTRACT

The present invention relates to N-carbomethoxy-N-methoxy-(2-chloromethyl)-aniline compounds of the formula I, wherein: n is 0, 1, 2 or 3, each $R^1$ is independently selected from halogen, $C_1$-$C_4$-alkyl, $C_1$-$C_4$-haloalkyl, $C_1$-$C_4$-alkoxy or C1-C4-haloalkoxy. The invention also relates to processes and intermediates for preparing such compounds of formula I. The invention furthermore relates to processes for preparing 2-(pyrazol-3'-yloxymethylene)-anilides in which compounds of formula I are applied as precursors.

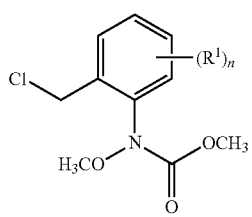

17 Claims, No Drawings

N-CARBOMETHOXY-N-METHOXY-(2-CHLOROMETHYL)-ANILINES, THEIR PREPARATION AND THEIR USE AS PRECURSORS FOR PREPARING 2-(PYRAZOL-3'-YLOXYMETHYLENE)-ANILIDES

This application is a National Stage application of International Application No. PCT/EP2011/054020, filed Mar. 17, 2011, which claims the benefit of U.S. Provisional Application No. 61/315,061, filed Mar. 18, 2010, the entire contents of which are hereby incorporated herein by reference. This application also claims priority under 35 U.S.C. §119 to European Patent Application No. 10156946.5, filed Mar. 18, 2010, the entire contents of which is hereby incorporated herein by reference.

The present invention relates to N-carbomethoxy-N-methoxy-(2-chloromethyl)-anilines and also to processes and intermediates for preparing these compounds. The invention furthermore relates to processes for preparing 2-(pyrazol-3'-yloxymethylene)-anilides in which N-carbomethoxy-N-methoxy-(2-chloromethyl)-anilines are used as precursors for preparing 2-(pyrazol-3'-yloxymethylene)-anilides.

The process for the commercial production of 2-(pyrazol-3'-yloxymethylene)-anilides is predominantly performed on the basis of a route outlined in WO96/01256 which includes reacting a 2-nitro-benzyl halide and a 3-hydroxypyrazole to the corresponding 2-(pyrazol-3'-yloxymethylene)-nitrobenzene. In subsequent steps the nitro group of the latter compound is derivatized to afford the corresponding N-carboalkoxy-N-alkoxy-aniline derivative, such as pyraclostrobine which is a prominent representative of this class of pesticides.

An alternative, more convergent approach for preparing 2-(pyrazol-3'-yloxymethylene)-anilides is described in WO93/015046. In its final step the two convergent reaction sequences are merged by coupling N-carbomethoxy-N-methoxy-(2-bromomethyl)-aniline with 1-(4-chlorophenyl)-3-hydroxy-pyrrazole. The N-carbomethoxy-N-methoxy-(2-bromomethyl)-aniline in turn is prepared by bromination of the corresponding toluene derivative. This bromination, however, is relatively non-selective and accompanied by several side-reactions such as core brominations and the formation of benzal bromide derivatives. In order to avoid excessive rates of side-products the reaction has to be quenched at incomplete conversion which results in a mixture comprising the starting material, the desired benzyl bromide, the corresponding benzal bromide and other side-products. The benzyl bromide compound can be isolated from this mixture only by column chromatography, which is not a viable option for a scaled-up synthesis. However, introducing the crude reaction mixture obtained after the bromination directly into the final step of the synthesis yields a 2-(pyrazol-3'-yloxymethylene)-anilide product that is contaminated with the aforementioned and further impurities. Studies performed by the inventors revealed that this crude product, again, can only be purified by elaborated methods that would hamper a cost-effective production scale synthesis.

It is the object of the present invention to provide a suitable precursor compound for the production of 2-(pyrazol-3'-yloxymethylene)-anilides which can be effectively coupled with 1-(4-chlorophenyl)-3-hydroxy-pyrrazole and which can be readily prepared in high purity to avoid the formation of undesirable side-products in the coupling reaction.

The object is achieved by the N-carbomethoxy-N-methoxy-(2-chloromethyl)-aniline compounds of the general formula I,

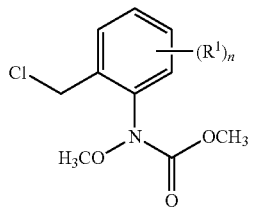

wherein:
n is 0, 1, 2 or 3, in particular 0,
each $R^1$ is independently selected from halogen, $C_1$-$C_4$-alkyl, $C_1$-$C_4$-haloalkyl, $C_1$-$C_4$-alkoxy or $C_1$-$C_4$-haloalkoxy,
and by the process for their preparation described in detail below.

The present invention provides a process for preparing 2-chloromethyl-aniline compounds of the general formula I as defined herein, which process comprises the following steps:

(a) reacting a benzyl bromide compound of formula II with a secondary amine of formula III,

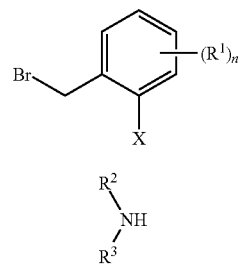

wherein n and $R^1$ are as defined for formula I,
X is $NO_2$ or the moiety $X^1$,

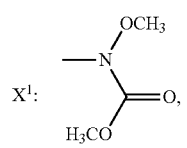

$R^2$ and $R^3$ are each independently of the other selected from $C_1$-$C_6$-alkyl, $C_3$-$C_6$-alkenyl, $C_2$-$C_6$-alkoxyalkyl, $C_3$-$C_8$-cycloalkyl, phenyl and benzyl, wherein the phenyl moieties of the last two radicals mentioned may or may not carry 1, 2 or 3 substituents independently selected from halogen, $C_1$-$C_4$-alkyl and $C_1$-$C_4$-alkoxy, or $R^2$ and $R^3$ together with the nitrogen atom to which they are bound form an unsubstituted or substituted 5-, 6- or 7-membered ring that in addition to nitrogen may also contain a further heteroatom O, S or N, to obtain a benzylamine compound of formula IV,

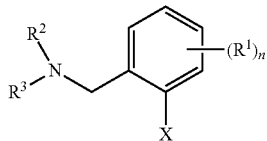

(IV)

wherein X, n, $R^1$, $R^2$ and $R^3$ are as defined herein before,
(b) if appropriate, converting the benzylamine compound of formula IV, wherein X is $NO_2$, to a benzylamine compound of formula IV with X being the moiety $X^1$, and
(c) reacting the benzylamine compound of formula IV, wherein X is the moiety $X^1$, with an acyl chloride of formula V,

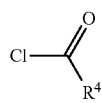

(V)

wherein:
$R^4$ is selected from $C_1$-$C_6$-alkoxy, $C_1$-$C_6$-haloalkoxy, $C_2$-$C_6$-alkenoxy, $C_2$-$C_6$-haloalkenoxy, $C_1$-$C_6$-alkyl, $C_1$-$C_6$-haloalkyl, $C_2$-$C_6$-alkenyl, $C_2$-$C_6$-haloalkenyl, benzyl, phenyl and benzoxy wherein the phenyl moieties of the last three radicals mentioned may or may not carry 1, 2 or 3 substituents independently selected from halogen, $C_1$-$C_4$-alkyl and $C_1$-$C_4$-alkoxy,
to obtain the 2-chloromethyl-aniline compound of formula I.

The processes and compounds of the invention are associated with several advantages. For instance, one process according to the invention provides 2-chloromethyl-anilines of the formula I in high purity and good yield without requiring excessive purification procedures, such as column chromatography. This has been achieved, in particular, by employing as direct precursor of compound I the benzylamine compound of formula IV, with the variable X being $X^1$, that is easily accessible from the benzyl bromide compound of formula II and that can be easily purified by simple means. It is a particular benefit of the invention that the benzylamine IV can be obtained in high purity, even if the benzyl bromide starting compound II contains large amounts of impurities. Thus, the process of the invention provides effective means for preparing pure starting materials for the preparation of fungicidally active 2-(pyrazol-3'-yloxymethylene)-anilide compound of formula X, as defined herein below, thereby avoiding a tedious purification at a late stage of the synthesis of the 2-(pyrazol-3'-yloxymethylene)-anilide X. According to another process of the invention 2-chloromethyl-aniline of the formula I is effectively coupled with a 1-(4-chlorophenyl)-3-hydroxy-pyrrazole compound of the formula XI, as defined herein below, to give the 2-(pyrazol-3'-yloxymethylene)-anilide X in high yield and excellent selectivity.

In the context of the present invention, the terms used generically are defined as follows:
The prefix $C_x$-$C_y$ denotes the number of possible carbon atoms in the particular case.
The term "halogen" denotes in each case fluorine, bromine, chlorine or iodine, especially chlorine or bromine.

The term "$C_1$-$C_4$-alkyl" denotes a linear or branched alkyl radical comprising from 1 to 4 carbon atoms, such as methyl, ethyl, propyl, 1-methylethyl (isopropyl), butyl, 1-methylpropyl (sec-butyl), 2-methylpropyl (isobutyl) or 1,1-dimethylethyl (tert-butyl).

The term "$C_1$-$C_6$-alkyl" denotes a linear or branched alkyl radical comprising from 1 to 6 carbon atoms. Examples are, as well as the radicals specified for $C_1$-$C_4$-alkyl, pentyl, hexyl, 1-methylbutyl, 2-methylbutyl, 1-ethylpropyl, 1,1-dimethylbutyl, 1,2-dimethylbutyl, 1-ethylbutyl, 1-methylpentyl, 2-methylpethyl, 3-methylpentyl and positional isomers thereof.

The term "cycloalkyl" denotes monocyclic saturated hydrocarbon groups having 3 to 6 ($C_3$-$C_6$-cycloalkyl), 3 to 8 ($C_3$-$C_8$-cycloalkyl) or 3 to 10 ($C_3$-$C_{10}$-cycloalkyl) carbon ring members, such as cyclopropyl, cyclobutyl, cyclopentyl, cyclohexyl, cycloheptyl, cyclooctyl, cyclononyl and cyclodecyl;

The term "$C_1$-$C_4$-haloalkyl", as used herein and in the haloalkyl units of $C_1$-$C_4$-haloalkoxy, describes straight-chain or branched alkyl groups having from 1 to 4 carbon atoms, where some or all of the hydrogen atoms of these groups have been replaced by halogen atoms. Examples thereof are chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3,3,3-trifluoroprop-1-yl, 1,1,1-trifluoroprop-2-yl, 3,3,3-trichloroprop-1-yl, heptafluoroisopropyl, 1-chlorobutyl, 2-chlorobutyl, 3-chlorobutyl, 4-chlorobutyl, 1-fluorobutyl, 2-fluorobutyl, 3-fluorobutyl, 4-fluorobutyl and the like.

The term "$C_1$-$C_4$-alkoxy" denotes straight-chain or branched saturated alkyl groups comprising from 1 to 4 carbon atoms, which are bound via an oxygen atom to the remainder of the molecule. Examples of $C_1$-$C_4$-alkoxy are methoxy, ethoxy, n-propoxy, 1-methylethoxy (isopropoxy), n-butoxy, 1-methylpropoxy (sec-butoxy), 2-methylpropoxy (isobutoxy) and 1,1-dimethylethoxy (tert-butoxy).

The term "$C_1$-$C_4$-haloalkoxy" describes straight-chain or branched saturated haloalkyl groups comprising from 1 to 4 carbon atoms, which are bound via an oxygen atom to the remainder of the molecule. Examples thereof are chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, 1,1,2,2-tetrafluoroethoxy, 1-chloro-1,2,2-trifluoroethoxy, pentafluoroethoxy, 3,3,3-trifluoroprop-1-oxy, 1,1,1-trifluoroprop-2-oxy, 3,3,3-trichloroprop-1-oxy, 1-chlorobutoxy, 2-chlorobutoxy, 3-chlorobutoxy, 4-chlorobutoxy, 1-fluorobutoxy, 2-fluorobutoxy, 3-fluorobutoxy, 4-fluorobutoxy and the like.

The term "$C_2$-$C_6$-alkoxyalkyl" refers to alkyl usually comprising 1 to 4 carbon atoms, wherein 1 carbon atom carries an alkoxy radical usually comprising 1 to 5, in particular 1 to 4, carbon atoms as defined above. Examples are $CH_2OCH_3$, $CH_2$—$OC_2H_5$, n-propoxymethyl, $CH_2$—$OCH(CH_3)_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)-ethyl, 2-(2-methylpropoxy)-ethyl, 2-(1,1-dimethylethoxy)-ethyl, 2-(methoxy)-propyl, 2-(ethoxy)-propyl, 2-(n-propoxy)-propyl, 2-(1-methylethoxy)-propyl, 3-(methoxy)-propyl, 3-(ethoxy)-propyl, 3-(n-propoxy)-propyl, 3-(1-methylethoxy)-propyl, 2-(methoxy)-butyl, 2-(ethoxy)-butyl, 3-(methoxy)-butyl, 3-(ethoxy)-butyl, 4-(methoxy)-butyl, 4-(ethoxy)-butyl and the like.

The term "$C_3$-$C_6$-alkenyl" denotes monounsaturated straight-chain or branched hydrocarbon radicals having 3 to 6 carbon atoms and a double bond in any position other than the α-β-position in respect to the attachment point. Examples thereof are 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like.

The term "$C_2$-$C_6$-alkenyl" describes monounsaturated straight-chain or branched hydrocarbon radicals having 2 to 6 carbon atoms and a double bond in any position. Examples for $C_2$-$C_6$-alkenyl include those given above for $C_3$-$C_6$-alkenyl and in addition also ethenyl, 1-propenyl, 1-methylethenyl, 1-butenyl, 1-methyl-1-propenyl, 2-methyl-1-propenyl, 1-pentenyl, 1-methyl-1-butenyl, 2-methyl-1-butenyl, 3-methyl-1-butenyl, 1,2-dimethyl-1-propenyl, 1-ethyl-1-propenyl, 1-hexenyl, 1-methyl-1-pentenyl, 2-methyl-1-pentenyl, 3-methyl-1-pentenyl, 4-methyl-1-pentenyl, 1,2-dimethyl-1-butenyl, 1,3-dimethyl-1-butenyl, 1,3-dimethyl-2-butenyl, 2,3-dimethyl-1-butenyl, 3,3-dimethyl-1-butenyl, 1-ethyl-1-butenyl, 2-ethyl-1-butenyl, 1-ethyl-2-methyl-1-propenyl, and the like.

The term "$C_2$-$C_6$-haloalkenyl" denotes alkenyl radicals as mentioned above which are partially or fully substituted by one or more halogen atom as mentioned above, in particular fluorine, chlorine and bromine.

The term "$C_2$-$C_6$-alkenoxy" denotes alkenyl radicals as mentioned above which are bound via an oxygen atom to the remainder of the molecule, for example 1-ethenyloxy, 1-propenyloxy, 2-propenyloxy, 1-methylethenyloxy, 1-butenyloxy, 2-butenyloxy, 3-butenyloxy, 1-methyl-1-propenyloxy, 2-methyl-1-propenyloxy, 1-methyl-2-propenyloxy, 2-methyl-2-propenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyl, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy, 1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-1-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenyloxy, 2,3-dimethyl-1-butenyloxy, 2,3-dimethyl-2-butenyloxy, 2,3-dimethyl-3-butenyloxy, 3,3-dimethyl-1-butenyloxy, 3,3-dimethyl-2-butenyloxy, 1-ethyl-1-butenyloxy, 1-ethyl-2-butenyloxy, 1-ethyl-3-butenyloxy, 2-ethyl-1-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-1-propenyloxy and 1-ethyl-2-methyl-2-propenyloxy and the like.

The term "$C_2$-$C_6$-haloalkenoxy" describes alkenoxy radicals as mentioned above which are partially or fully substituted by one or more halogen atom as mentioned above, in particular fluorine, chlorine and bromine.

The term "$C_1$-$C_4$-alkoxycarbonyl" denotes alkoxy radicals having from 1 to 4 carbon atoms which are bound via a carbonyl group to the remainder of the molecule. Examples thereof are methoxycarbonyl, ethoxycarbonyl, propoxycarbonyl, isopropoxycarbonyl, n-butoxycarbonyl, sec-butoxycarbonyl, isobutoxycarbonyl and tert-butoxycarbonyl.

The term "aryl" denotes carbocyclic aromatic radicals having from 6 to 14 carbon atoms. Examples thereof comprise phenyl, naphthyl, fluorenyl, azulenyl, anthracenyl and phenanthrenyl. Aryl is preferably phenyl or naphthyl, and especially phenyl.

The term "$C_1$-$C_4$-alkylthio "($C_1$-$C_4$-alkylsulfanyl: $C_1$-$C_4$-alkyl-S—)" denotes straight-chain or branched saturated alkyl radicals having 1 to 4 carbon atoms which are bound via a sulfur atom to the remainder of the molecule. Examples for $C_1$-$C_4$-alkylthio include methylthio, ethylthio, propylthio, 1-methylethylthio, butylthio, 1-methylpropylthio, 2-methylpropylthio and 1,1-dimethylethylthio.

Hereinafter compound of the formula IV, where X is a radical $X^1$ are referred to as compounds of the formula IV'.

The remarks made below regarding preferred embodiments of the process according to the invention, especially regarding preferred meanings of the variables of the different reactants and products and of the reaction conditions of the process, apply either taken alone or, more particularly, in any conceivable combination with one another.

In the compounds of formulae I, II, IV and IV' n is preferably 0, 1 or 2 and especially preferably 0 or 1, in particular 0. When n is 1, $R^1$ is preferably in the para or meta position to the attachment point of the nitro group or the radical $X^1$, respectively.

In the compounds of formulae I, II, IV and IV' $R^1$ is preferably, if present, chlorine, bromine, $C_1$-$C_2$-alkyl, $C_1$-$C_2$-haloalkyl, $C_1$-$C_2$-alkoxy or $C_1$-$C_2$-haloalkoxy. $R^1$ is more preferably chlorine, $C_1$-$C_2$-alkyl or $C_1$-$C_2$-haloalkyl and even more preferably chlorine, methyl or halomethyl. Specifically, $R^1$ is 4-Cl, 3-Cl, 4-methyl, 3-methyl, 4-methoxy, 3-methoxy, 3-chloromethyl, 4-chloromethyl, 4-trifluoromethyl, 3-trifluoromethyl, 3-chloromethoxy, 4-chloromethoxy, 4-trifluoromethoxy, 3-trifluoromethoxy, 3,4-$C_{12}$, 3,4-dimethyl or 3,4-dimethoxy. The statements of position relate to the 1-position of the nitro group or the radical $X^1$, respectively, and the 6-position of the methylene substituent.

In the compounds of formulae III, IV and IV' $R^2$ and $R^3$ are preferably either, independently of one another, selected from $C_1$-$C_4$-alkyl, $C_2$-$C_4$-alkoxyalkyl, $C_3$-$C_8$-cycloalkyl and benzyl, wherein the phenyl moiety of the benzyl radical may or may not carry 1, 2 or 3 substituents independently selected from halogen, $C_1$-$C_2$-alkyl and $C_1$-$C_2$-alkoxy, or $R^2$ and $R^3$ together with the nitrogen atom to which they are bound form a saturated or partially unsaturated 5-, 6- or 7-membered ring that in addition to nitrogen may also contain a further heteroatom O, S or N. More preferred are $R^2$ and $R^3$ that are either, independently of one another, selected from $C_1$-$C_3$-alkyl, $C_2$-$C_4$-alkoxyalkyl and $C_3$-$C_8$-cycloalkyl, or together with the nitrogen atom to which they are bound form a saturated 5- or 6-membered ring that in addition to nitrogen may also contain a further heteroatom O or N. Specifically, $R^2$ and $R^3$ are both methyl, ethyl or propyl, or together with the nitrogen atom to which they are bound form a pyrrolidinyl moiety, a piperidinyl moiety or a morpholinyl moiety.

In the compound of formula V $R^4$ is preferably $C_2$-$C_6$-alkoxy, $C_2$-$C_6$-haloalkoxy, $C_1$-$C_6$-alkyl, $C_1$-$C_6$-haloalkyl, phenyl or benzoxy, wherein the phenyl moieties of the last two radicals mentioned may or may not carry 1, 2 or 3 substituents independently selected from halogen, $C_1$-$C_2$-alkyl and $C_1$-$C_2$-alkoxy. $R^4$ is more preferably $C_2$-$C_5$-alkoxy, $C_2$-$C_5$-haloalkoxy, $C_1$-$C_4$-alkyl or $C_1$-$C_4$-haloalkyl and even more preferably $C_2$-$C_4$-alkoxy or $C_2$-$C_4$-haloalkoxy. In particular $R^4$ is ethoxy, propoxy, n-butoxy or iso-butoxy and specifically ethoxy or iso-butoxy.

The reactions of the invention as described hereinafter are performed in reaction vessels customary for such reactions, the reaction being carried out in a continuous, semicontinuous or batchwise manner. In general, the particular reactions will be carried out under atmospheric pressure. The reactions may, however, also be carried out under reduced or elevated pressure.

The conversion in step (a) of the process according to the invention for preparing 2-chloromethyl-aniline compounds I is an amination reaction resulting in the formation of the tertiary benzylamine compound IV. The conversion is effected by reacting the starting compounds, i.e. the secondary amine III and the benzyl bromide compound II, and optionally an auxiliary base, preferably in a solvent, under suitable reaction conditions.

Preferred secondary amines III are selected from di-($C_1$-$C_4$-alkyl)-amines, di-($C_2$-$C_4$-alkoxyalkyl)-amines, $C_2$-$C_4$-alkoxyalkyl-$C_1$-$C_4$-alkyl-amines, $C_3$-$C_7$-cycloalkyl-$C_1$-$C_4$-alkyl-amines, benzyl-$C_1$-$C_4$-alkyl-amines and five- six- or seven-membered saturated or partially unsaturated heterocycles which contain as ring members one nitrogen atom (as N—H) and optionally one or two additional heteroatoms selected from oxygen and nitrogen (as N or N—R with R being $C_1$-$C_4$-alkyl). The secondary amines III are more preferably selected from dimethylamine, diethylamine, dipropylamine, methylethylamine, methylpropylamine, ethylpropylamine, pyrrolidine, oxazolidine, dihydropyrrole, piperidine, piperazine, dihydropyridine and morpholine, and especially from dimethylamine, diethylamine, pyrrolidine, piperidine and morpholine.

The reactants can in principle be contacted with one another in any desired sequence. For example, the benzyl bromide compound II, if appropriate in dissolved or dispersed form, can be initially charged and admixed with the secondary amine III or, conversely, the secondary amine III, if appropriate in dissolved or dispersed form, can be initially charged and admixed with the benzyl bromide compound II. Alternatively, the two reactants can also be added simultaneously to the reaction vessel. The optional auxiliary base can be added before or after the addition of one of the reactants or else together with one of the reactants, either in a solvent or in bulk.

It has been found to be appropriate to initially charge the reaction vessel with the benzyl bromide compound II as such, in dispersed form or preferably in dissolved form, and then add the secondary amine III and optionally the auxiliary base.

The secondary amine III and the auxiliary base, if applicable, are independently of one another employed as such or in dissolved form.

Suitable solvents for dissolving or dispersing the reactants are preferably organic solvents that are inert toward the reactants. The choice of the solvent for the conversion in step (a) therefore depends on the particular reactants and reaction conditions selected in an individual case. In general, useful organic solvents here include, for example, aliphatic $C_3$-$C_8$-ethers, such as diethyl ether, diisopropyl ether, dibutyl ether, isobutyl methyl ether, tert-butyl methyl ether, tert-butyl ethyl ether, 1,2-dimethoxyethane (DME), diethylene glycol dimethyl ether (diglyme), carboxylic esters, e.g. ethyl acetate, propyl acetate or ethyl propionate, halogenated aliphatic hydrocarbons such as methylene chloride, trichloromethane, dichloroethane and trichloroethane, aliphatic alcohols, such as methanol, ethanol, n-propanol, isopropanol, n-butanol, isobutanol and tert-butanol, aliphatic hydrocarbons, such as pentane, hexane, heptane and octane, and also petroleum ether, cycloaliphatic hydrocarbons, such as cyclopentane and cyclohexane, alicyclic $C_3$-$C_6$-ethers, such as tetrahydrofuran (THF), tetrahydropyran, 2-methyltetrahydrofuran, 3-methyltetrahydrofuran and 1,4-dioxane, aromatic hydrocarbons, such as benzene, chlorobenzene, anisole, toluene, the xylenes and mesitylene, short-chain ketones, such as acetone, ethyl methyl ketone and isobutyl methyl ketone, amides such as dimethylformamide (DMF), dimethylacetamide (DMA) and N-methylpyrrolidone (NMP), dimethyl sulfoxide (DMSO), acetonitrile, 1,3-dimethyl imidazolidin-2-one, 1,2-dimethyl tetrahydro-2(1H)-pyrimidine, or mixtures of these solvents with one another.

Preferably the organic solvent for the conversion in step (a) is selected from halogenated aliphatic hydrocarbons, such as methylene chloride, aromatic hydrocarbons, such as chlorobenzene or toluene, and mixtures thereof. For instance, initially the benzyl bromide compound II may be charged to the reaction vessel solved in a halogenated aliphatic hydrocarbon and then the secondary amine III, the optional auxiliary base and additional solvent, such as an aromatic hydrocarbon, may be added separately, or in the form of a partial or complete mixture.

The total amount of the solvent used in step (a) of the process according to the invention is typically in the range from 200 to 6000 g/mol and preferably in the range from 500 to 5000 g/mol, based in each case on the benzylbromide compound II.

In a preferred embodiment of the invention, in step (a), the secondary amine III is used in an amount of 1.2 to 3.2 mol, more preferably 1.7 to 2.7 mol and especially 1.9 to 2.4 mol, based in each case on 1 mol of the benzyl bromide compound II.

In another preferred embodiment of the invention, the reaction in step (a) is carried out with 0.8 to 2.5 mol, more preferably 0.9 to 1.7 mol and especially 0.9 to 1.3 mol of the secondary amine III in presence of 0.1 to 2.5 mol, more preferably 0.7 to 1.7 mol and especially 0.8 to 1.3 mol of an auxiliary base, based in each case on 1 mol of the benzyl bromide compound II. This embodiment is particularly preferred in case the variable X of the benzyl bromide compound II is a moiety as defined herein before. It is assumed that by reducing the amount of the secondary amine III closer to the 1 molar equivalent in relation to compound II the possible attack of the amine III on the moiety $X^1$ is suppressed.

The choice of auxiliary base that may be employed in the conversion in step (a) depends on several factors, such as the reactivity of the reactants used, and can be determined by the person skilled in the art in the individual case, for example by simple preliminary tests. In general the base is selected from bases commonly known to be useful for similar reactions, for instance inorganic compounds such as alkali metal and alkaline earth metal hydroxides, e.g. lithium hydroxide, sodium hydroxide, potassium hydroxide and calcium hydroxide, alkali metal and alkaline earth metal oxides, e.g. lithium oxide, sodium oxide, calcium oxide and magnesium oxide, alkali metal and alkaline earth metal carbonates, e.g. potassium carbonate and calcium carbonate, and also alkali metal hydrogen carbonates, e.g. sodium hydrogen carbonate, alcoholates, in particular alkali metal and alkaline earth metal alkoxides, e.g. sodium methoxide, sodium ethoxide, potassium ethoxide, potassium tert-butoxide and dimethoxy-magnesium, and in addition organic bases, e.g. tertiary amines such as trimethylamine, triethylamine, diisopropylethylamine and N-methylpiperidine, pyridine, substituted pyridines such as collidine, lutidine and 4-dimethylaminopyridine, as well as bicyclic amines such as diaza-bicyclo[4.3.0]-5-nonene (DBN) and 1,8-diaza-bicyclo[5.4.0]-7-undecene (DBU). In this context the auxiliary base is preferably selected from tertiary amines, in particular triethylamine, alkali metal carbonates, in particular sodium carbonate and potassium carbonate, alkali metal hydrogen carbonates, in particular sodium hydrogen carbonate and potassium hydrogen carbonate, and alkali metal hydroxides, in particular sodium hydroxide and potassium hydroxide, and specifically selected from triethylamine, sodium carbonate and potassium carbonate.

In general, step (a) is performed under temperature control. The reaction is typically effected in a closed or open reaction vessel with stirring apparatus. The reaction temperature of step (a) depends on several factors, for example the reactivity of the reactants used, and can be determined by the person skilled in the art in the individual case, for example by simple preliminary tests. In general, the conversion in step (a) is performed at a temperature in the range from −20 to 150° C., preferably in the range from 0 to 100° C., more preferably in the range from 5 to 70° C. and specifically in the range from 10 to 50° C. Depending on the solvent used, the reaction temperature and on whether the reaction vessel possesses a vent, a pressure of generally 1 to 5 bar and preferably of 1 to 3 bar is established during the reaction.

The work-up of the reaction mixtures obtained in the amination reaction of step (a) and the isolation of the benzylamine compound IV are effected in a customary manner, for example by an aqueous extractive work-up or by removing the solvent, for example under reduced pressure. Generally, benzylamine compounds IV are obtainable in sufficient purity by applying such measures or a combination thereof. Thus, additional purification steps, in particular elaborated ones such as chromatography or distillation are usually not necessary. If desired, however, further purification can be effected by methods commonly used in the art.

Preferably the reaction mixture from step (a), for work-up, is treated with an aqueous acidic solution, such as aqueous sulfuric acid, preferably at a reduced temperature of about −10 to 10° C., and then the aqueous phase is extracted more than once with a suitable, essentially water-immiscible organic solvent, such as methylene chloride. Afterwards the aqueous phase is neutralized with an aqueous base solution, such as potassium carbonate, and then the aqueous phase is extracted more than once with a suitable, essentially water-immiscible organic solvent, such as methylene chloride. The combined organic phases are washed, e.g. with water and/or brine, dried and concentrated. The product thus isolated can subsequently be retained for uses or sent directly to a use, for example used in a further reaction step, or be purified further beforehand.

If the benzylamine compound IV obtained from step (a) carries a nitro group as variable X, it is converted in step (b) into the corresponding benzylamine compound IV having a moiety $X^1$, as defined herein before, in position X. The procedures for accomplishing this conversion of step (b) are discussed in more detail herein below.

In step (c) of the process according to the invention for preparing 2-chloromethyl-aniline compounds I the benzylamine compound IV with the variable X being a moiety $X^1$ (herein also denoted as benzylamine compound IV') is transferred to the 2-chloromethyl-aniline compound of formula I. The reaction is effected by reacting the benzylamine compound IV' with the acyl chloride of the formula V preferably in a solvent under suitable reaction conditions. Step (c) can be performed e.g. by analogy to WO 97/14688.

The acyl chlorides V are preferably selected from $C_1$-$C_6$-alkyl chloroformates, in particular $C_2$-$C_6$-alkyl chloroformates, $C_1$-$C_6$-haloalkyl chloroformates, in particular $C_2$-$C_4$-haloalkyl chloroformates, $C_1$-$C_6$-alkyl carboxylic acid chlorides, $C_1$-$C_6$-haloalkyl carboxylic acid chlorides, benzyl chloroformates and benzoic acid chlorides, wherein the phenyl moieties of the last two compound groups mentioned may or may not carry 1, 2 or 3 substituents independently selected from halogen, $C_1$-$C_2$-alkyl and $C_1$-$C_2$-alkoxy. More preferably the acyl chlorides V are selected from $C_2$-$C_5$-alkyl chloroformates, in particular ethyl chloroformate and iso-butyl chloroformate, and $C_1$-$C_4$-alkyl carboxylic acid chlorides, in particular acetic acid chloride, propionic acid chloride, n-butyric acid chloride or iso-butyric acid chloride.

For effecting the reaction of the benzylamine compound IV' with the acyl chlorides V the reactants can in principle be contacted with one another in any desired sequence. For example, the benzylamine compound IV', if appropriate in dissolved or dispersed form, can be initially charged and admixed with the acyl chloride V or, conversely, the acyl chloride V, if appropriate in dissolved or dispersed form, can be initially charged and admixed with the benzylamine compound IV'. Alternatively, the two reactants can also be added simultaneously to the reaction vessel.

It has been found to be appropriate to initially charge the reaction vessel with the benzylamine compound IV' in dispersed form or preferably in dissolved form, and then add the acyl chloride V. The acyl chloride V is employed as such or in dispersed or dissolved form.

Suitable solvents for dissolving or dispersing the reactants depend in the individual case on the selection of the particular reactants and reaction conditions. In general, aprotic organic solvents are advantageous for the reaction of a compound IV' with a compound V. Useful aprotic organic solvents here include, for example, aliphatic $C_3$-$C_8$-ethers, such as diethyl ether, diisopropyl ether, dibutyl ether, isobutyl methyl ether, tert-butyl methyl ether, tert-butyl ethyl ether, 1,2-dimethoxyethane (DME), diethylene glycol dimethyl ether (diglyme), carboxylic esters, e.g. ethyl acetate, propyl acetate or ethyl propionate, halogenated aliphatic hydrocarbons such as methylene chloride, trichloromethane, dichloroethane and trichloroethane, aliphatic hydrocarbons, such as pentane, hexane, heptane and octane, and also petroleum ether, cycloaliphatic hydrocarbons, such as cyclopentane and cyclohexane, alicyclic $C_3$-$C_6$-ethers, such as tetrahydrofuran (THF), tetrahydropyran, 2-methyltetrahydrofuran, 3-methyltetrahydrofuran and 1,4-dioxane, aromatic hydrocarbons, such as benzene, chlorobenzene, anisole, toluene, the xylenes and mesitylene, short-chain ketones, such as acetone, ethyl methyl ketone and isobutyl methyl ketone, amides such as dimethylformamide (DMF), dimethylacetamide and N-methylpyrrolidone (NMP), dimethyl sulfoxide (DMSO), acetonitrile, 1,3-dimethyl imidazolidin-2-one, 1,2-dimethyl tetrahydro-2(1H)-pyrimidine, or mixtures of these solvents with one another.

Preferably the solvent for the conversion in step (c) is selected from suitable aprotic organic solvents that are inert towards the reactants, and in particular from acetonitrile, DMF, aromatic hydrocarbons, especially toluene, halogenated aliphatic hydrocarbons, especially methylene chloride, and mixtures thereof.

For the conversion in step (c) preference is given to using solvents which are essentially anhydrous, i.e. have a water content of less than 1000 ppm and especially not more than 100 ppm.

The total amount of the solvent used in step (c) of the process according to the invention is typically in the range from 500 to 7000 g/mol and preferably in the range from 1000 to 6000 g/mol, based in each case on the benzylamine compound IV'.

In step (c) the acyl chloride V is preferably used in an amount of 0.8 to 3.0 mol, more preferably 0.9 to 2.5 mol and in particular 1.0 to 2.0 mol, based in each case on 1 mol of the benzylamine compound IV'.

In general, step (c) is performed under temperature control. The reaction is typically effected in a closed or open reaction vessel with stirring apparatus. The reaction temperature of step (c) depends on several factors, for example the reactivity of the reactants used, and can be determined by the person skilled in the art in the individual case, for example by simple preliminary tests. In general, the conversion in step (c) is performed at a temperature in the range from −20 to 150° C., preferably in the range from 0 to 100° C., more preferably in the range from 5 to 70° C. and specifically in the range from 10 to 50° C. Depending on the solvent used, the reaction temperature and on whether the reaction vessel possesses a vent, a pressure of generally 1 to 5 bar and preferably of 1 to 3 bar is established during the reaction.

The work-up of the reaction mixtures obtained in the conversion of step (c) and the isolation of the 2-chloromethyl-aniline compound I are effected in a customary manner, for example by an aqueous extractive work-up or by removing the solvent, for example under reduced pressure. Generally, 2-chloromethyl-aniline compounds I are obtainable in sufficient purity by applying such measures or a combination thereof. Thus, additional purification steps, in particular elaborated ones such as chromatography or distillation are not required. If desired, however, further purification can be effected by methods commonly used in the art.

In a preferred embodiment of the invention, the reaction mixture from step (c), for work-up, is diluted with a suitable, essentially water-immiscible organic solvent, such as methylene chloride or methyl tert-butyl ether, and treated with an aqueous solution, in particular water. The dilution may be effected before, after or simultaneously with the aqueous treatment. Preferably the organic solvent is added to the reaction mixture before the addition of the aqueous solution. The aqueous phase is then extracted more than once with the essentially water-immiscible organic solvent. Afterwards the combined organic phases are washed, e.g. with water and/or brine, dried and concentrated. The product thus isolated can subsequently be retained for uses or sent directly to a use, for example used in a further reaction step, or be purified further beforehand.

If the variable X in the starting compound of the formula II is a $NO_2$ group, step (b) is performed to convert the $NO_2$ group of the benzylamine IV into the radical $X^1$. The conversion of the $NO_2$ group into the radical $X^1$ can be achieved by standard methods of organic chemistry, e.g. by the methods described in EP 0624155 and WO 96/01256. In a particular embodiment of the invention the conversion in step (b) comprises the following sub-steps:

(b-1) reducing a benzylamine compound IV, wherein X is $NO_2$, to obtain a hydroxylamine compound of formula IVa, wherein the variables n, $R^1$, $R^2$ and $R^3$ are as defined herein before,

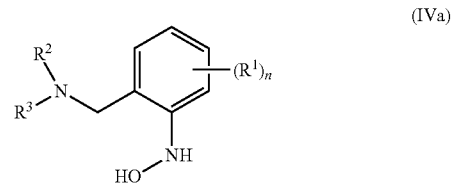

(IVa)

(b-2) acylating the hydroxylamine compound IVa with a methyl haloformate to obtain a hydroxycarbamate compound of formula IVb, wherein the variables n, $R^1$, $R^2$ and $R^3$ are as defined herein before,

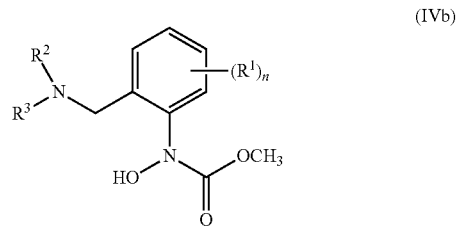

(IVb)

(b-3) methylating the hydroxycarbamate compound IVb to obtain the benzylamine compound IV'.

The variable n in the compounds of formulae IVa and IVb is preferably 0, 1 or 2 and especially preferably 0 or 1. When n is 1, $R^1$ is preferably in the para or meta position to the attachment point of the derivatized amino group.

The radical $R^1$ in the compounds of formulae IVa and IVb is preferably, if present, chlorine, bromine, $C_1$-$C_2$-alkyl, $C_1$-$C_2$-haloalkyl, $C_1$-$C_2$-alkoxy or $C_1$-$C_2$-haloalkoxy. $R^1$ is more preferably chlorine, $C_1$-$C_2$-alkyl or $C_1$-$C_2$-haloalkyl and even more preferably chlorine, methyl or halomethyl. Specifically, $R^1$ is 4-Cl, 3-Cl, 4-methyl, 3-methyl, 4-methoxy, 3-methoxy, 3-chloromethyl, 4-chloromethyl, 4-trifluoromethyl, 3-trifluoromethyl, 3-chloromethoxy, 4-chloromethoxy, 4-trifluoromethoxy, 3-trifluoromethoxy, 3,4-$Cl_2$, 3,4-dimethyl or 3,4-dimethoxy. The statements of position relate to the 1-position of the derivatized amino group and the 6-position of the aminomethyl substituent.

Radicals $R^2$ and $R^3$ in the compounds of formulae IVa and IVb are preferably either, independently of one another, selected from $C_1$-$C_4$-alkyl, $C_2$-$C_4$-alkoxyalkyl, $C_3$-$C_8$-cycloalkyl and benzyl, wherein the phenyl moiety of the benzyl radical may or may not carry 1, 2 or 3 substituents independently selected from halogen, $C_1$-$C_2$-alkyl and $C_1$-$C_2$-alkoxy, or $R^2$ and $R^3$ together with the nitrogen atom to which they are bound form a saturated or partially unsaturated 5-, 6- or 7-membered ring that in addition to nitrogen may also contain a further heteroatom O, S or N. More preferred are $R^2$ and $R^3$ that are either, independently of one another, selected from $C_1$-$C_3$-alkyl, $C_2$-$C_4$-alkoxyalkyl and $C_3$-$C_8$-cycloalkyl, or together with the nitrogen atom to which they are bound form a saturated 5- or 6-membered ring that in addition to nitrogen may also contain a further heteroatom O or N. Specifically, $R^2$ and $R^3$ are both methyl, ethyl or propyl, or together with the nitrogen atom to which they are bound form a pyrrolidinyl moiety, a piperidinyl moiety or a morpholinyl moiety.

In step (b-1) the benzylamine compound IV that is ring-substituted by a nitro group is reduced to the corresponding N-hydroxylamine compound IVa. This reaction can be performed in an analogous manner to methods known from the literature for reducing nitroarenes to arylhydroxylamines, for example by using the following reagents: Raney nickel/hydrazine (cf. N. R. Ayyangar, K. C. Brahme, U. R. Kalkote, K. V. Srinivasan, Synthesis 1984, 938), rhodium on carbon/hydrazine or palladium/phosphonic acid (cf. I. D. Entwistle, T. Gilkerson, R. A. W. Johnstone, R. P. Telford, Tetrahedron 1978, 34, 213), tin(II) chloride (cf. D. Shi, G. Dou, Y. Zhou, Synthesis 2008, 2000), zinc/ammonium chloride (cf. S. Blechert, Liebigs Ann. Chem. 1985, 673), bismuth chloride/potassium boronate (cf. P.-D. Ren, X.-W. Pan, Q.-H. Jin, Z.-P. Yao, Synth. Commun. 1997, 27, 3497) or hydrogen/palladium on carbon (cf. EP 085890).

The conversion in step (b-1) is however preferably effected by a heterogeneous hydrogenation employing a platinum or palladium catalyst, whereas in either case the metal is usually supported on carbon, in the presence of an amine, as described for example in GB 1458753, U.S. Pat. No. 3,992,395, GB 1428226, GB 1388523 and GB 1092027. Particularly preferred variants of this hydrogenation method for accomplishing step (b-1) are those described in WO 96/22967 and WO 99/12911. According to WO 96/22967 the amine is a morpholine compound which usually also functions as solvent, while according to WO 99/12911 the reaction is carried out in the presence of an aliphatic amine in an inert, aprotic solvent.

After completion of the reaction the catalyst is removed, e.g. by filtration, and the thus obtained crude N-hydroxylamine compound IVa may or may not be further purified, e.g. by distillation or chromatography. Preferably, the N-hydroxylamine compound IVa is employed in subsequent step (b-2) as crude product.

In step (b-2) the N-hydroxylamine compound IVa is acylated under alkaline conditions with a methyl haloformate, in particular methyl chloroformate, according to methods known in the art to obtain a hydroxycarbamate compound of formula IVb.

The acylation in step (b-2) is customarily carried out at a temperature of from −20 to 80° C., preferably from −10 to 30° C.

Preferably step (b-2) is carried out in an aprotic solvent.

Suitable aprotic solvents include those described herein before regarding the conversion of step (c) and are preferably selected from halogenated aliphatic hydrocarbons, in particular methylene chloride, aromatic hydrocarbons, in particular toluene, aliphatic $C_3$-$C_8$-ethers, in particular tert-butyl methyl ether, carboxylic esters, in particular ethyl acetate, and mixtures thereof.

Suitable bases generally include those described herein before regarding the conversion of step (a) and are preferably selected from alkali metal carbonates, in particular sodium carbonate and potassium carbonate, alkali metal hydrogen carbonates, in particular sodium hydrogen carbonate and potassium hydrogen carbonate, and alkali metal hydroxides, in particular sodium hydroxide and potassium hydroxide, and specifically selected from sodium hydrogen carbonate, potassium carbonate and aqueous sodium hydroxide solution.

The acylation in step (b-2) is preferably effected in a two-phase system consisting of an aqueous solution of a hydroxide, hydrogen carbonate or carbonate of an alkali metal or an alkaline earth metal and an organic phase consisting of the aforementioned organic solvent. The reaction may or may not be carried out in the presence of a phase transfer catalyst. Suitable phase transfer catalysts in this case are, for example, ammonium halides, e.g. benzyltriethylammonium chloride, benzyltributylammonium bromide, tetrabutylammonium chloride and hexadecyltrimethylammonium bromide, tetrafluoroborates, e.g. tetrabutylammonium tetrafluoroborate, or phosphonium halides, e.g. tetrabutylphosphonium chloride and tetraphenylphosphonium bromide.

It is usually advantageous to carry out the acylation in step (b-2) as follows: a solution of the N-hydroxylamine compound IVa in the aprotic organic solvent is first treated with a base, preferably by adding an aqueous solution of one of the aforementioned preferred inorganic bases. To the thus obtained biphasic mixture is then added the methyl haloformate, preferably at a reduced temperature of form −10 to 10° C. The reaction is continued until complete or almost complete conversion.

The work-up of the reaction mixture obtained in step (b-2) and the isolation of the hydroxycarbamate compound IVb are effected in a customary manner, for example by an aqueous extractive work-up, by removing the solvent, for example under reduced pressure, or by a combination of these measures. Further purification can be effected, for example, by distillation or chromatography.

Preferably, in case a biphasic reaction medium is employed, the reaction mixture from step (b-2) is worked up by extracting the aqueous phase more than once with a suitable, essentially water-immiscible organic solvent, such as methylene chloride. The combined organic phases are then optionally washed with an aqueous solution, dried and concentrated.

In subsequent step (b-3) the hydroxycarbamate compound IVb obtained in step (b-2) is usually employed as the crude product or after an additional purification step.

In step (b-3) the hydroxycarbamate compound IVb is converted to the benzylamine compound IV by exposure to basic conditions and reaction with a methylating agent.

In general, suitable methylating agents are those commonly used in the art for similar reactions. However, preferred methylating agents for the conversion in step (b-3) are methyl iodide and dimethyl sulfate.

The conversion in step (b-3) is customarily carried out in an aprotic organic solvent that is essentially anhydrous, i.e. has a water content of less than 1000 ppm and especially not more than 100. Suitable aprotic solvents include those described herein before regarding the conversion of step (c) and are preferably selected from halogenated aliphatic hydrocarbons, in particular methylene chloride, aromatic hydrocarbons, in particular toluene, aliphatic $C_3$-$C_8$-ethers, in particular tert-butyl methyl ether, alicyclic $C_3$-$C_6$-ethers, in particular THF, and mixtures thereof.

In general the base is selected from bases commonly known to be useful for similar reactions, for instance inorganic compounds such as alkali metal and alkaline earth metal hydroxides, e.g. lithium hydroxide, sodium hydroxide, potassium hydroxide and calcium hydroxide, alkali metal and alkaline earth metal oxides, e.g. lithium oxide, sodium oxide, calcium oxide and magnesium oxide, alkali metal and alkaline earth metal hydrides, e.g. lithium hydride, sodium hydride, potassium hydride and calcium hydride, alkali metal amides, e.g. lithium amide, sodium amide and potassium amide, alkali metal and alkaline earth metal carbonates, e.g.

lithium carbonate and calcium carbonate, and also alkali metal hydrogen carbonates, e.g. sodium hydrogen carbonate, organometallic compounds, in particular alkali metal alkyls, e.g. methyllithium, butyllithium and phenyllithium, alkyl-magnesium halides, e.g. methylmagnesium chloride, amides, in particular alkali metal alkylamides, e.g. lithium diisopropylamide, alkali metal bis(trimethylsilyl)amides, e.g. sodium bis(trimethylsilyl)amide and also alcoholates, in particular alkali metal and alkaline earth metal alkoxides, e.g. sodium methoxide, sodium ethoxide, potassium ethoxide, potassium tert-butoxide and dimethoxy-magnesium, and in addition organic bases, e.g. tertiary amines such as trimethylamine, triethylamine, triisopropylethylamine and N-methylpiperidine, pyridine, substituted pyridines such as collidine, lutidine and 4-dimethylaminopyridine, as well as bicyclic amines such as diaza-bicyclo[4.3.0]-5-nonene (DBN) and 1,8-diaza-bicyclo[5.4.0]-7-undecene (DBU). In this context the base is preferably selected from alkali metal hydroxides in particular sodium hydroxide and potassium hydroxide, alkali metal carbonates, in particular sodium carbonate and potassium carbonate, alkali metal and alkaline earth metal hydrides, in particular sodium hydride and potassium hydride, alkali metal alkylamides, in particular lithium diisoproylamide, alkali metal bis(trimethylsilyl)amides, in particular lithium bis(trimethylsilyl)amide, sodium bis(trimethylsilyl)amide and potassium bis(trimethylsilyl)amide, and specifically selected from sodium hydride, potassium hydride, lithium diisoproylamide and sodium bis(trimethylsilyl)amide.

The methylation in step (b-3) is preferably effected by initially treating the hydroxycarbamate compound IVb with the base. To this end, typically a solution of the hydroxycarbamate compound IVb is added to the dispersed or solved base at a temperature of from −30 to 20° C., preferably from −10 to 10° C. Afterwards the methylating agent is added and the obtained mixture is kept at a temperature of from −10 to 50° C., preferably from 0 to 30° C. until complete or almost complete conversion.

The work-up of the reaction mixture obtained in step (b-3) and the isolation of the benzylamine compound IV are effected in a customary manner, for example by an aqueous extractive work-up, by removing the solvent, for example under reduced pressure, or by a combination of these measures. Further purification can be effected, for example, by distillation or chromatography.

Preferably, for work-up, water is added to the reaction mixture from step (b-3) in order to quench the reaction, usually subsequent to diluting the mixture with a suitable, essentially water-immiscible organic solvent, such as methylene dichloride. The aqueous phase is extracted more than once with the water-immiscible organic solvent and the combined organic phases are then optionally washed with an aqueous solution, dried and concentrated.

The benzyl bromide starting compounds of the formula II are known in the art or they can be prepared by analogy to standard methods of organic chemistry, e.g. by the methods described in Houben-Weyl, "Methods of organic Chemistry", vol. 5/4, page 331 ff (1960). It is a particular benefit of the present invention that there is no particular requirement with regard to the purity of the employed benzyl bromide II. For instance, the benzyl bromide II may have a purity of less than 80% by weight, e.g. from 10 to 80% by weight, in particular from 15 to 50% by weight, based on the total amount of benzyl bromide II and impurities. Typical impurities include the corresponding benzal bromide IIa, as depicted below, the toluene compound of formula VI or of formula VII and core brominated side-products of II, IIa and VI or VII (i.e. compounds, where n is different from 0 and $R^1$ includes Br).

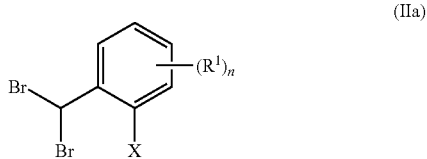

(IIa)

In yet another aspect of the invention the benzyl bromide compound II employed in step (a) of the process for preparing 2-chloromethyl-aniline compounds I is prepared by a method comprising the following steps:

(i) converting a 2-nitro-toluene compound of formula VI,

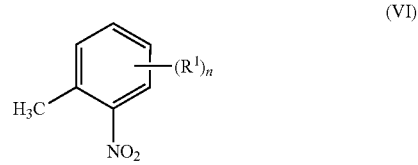

(VI)

wherein the variables n and $R^1$ are as defined herein before, to a benzyl bromide compound of formula II,

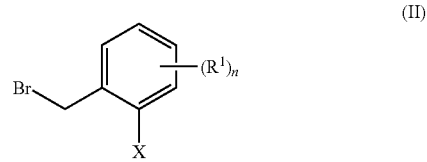

(II)

wherein the variables n, $R^1$, and X are as defined herein before, either, in case X is a moiety $X^1$ as defined herein before, by the following sub-steps (i-a1) and (i-a2):

(i-a1) converting 2-nitro-toluene compound VI to a compound of formula VII,

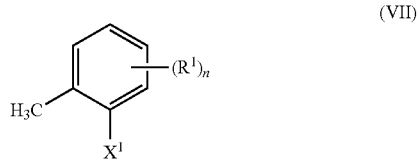

(VII)

wherein $X^1$, n and $R^1$ are as defined herein before, (i-a2) brominating the side-chain of compound VII to obtain a benzyl bromide II with X being a moiety $X^1$, or, in case X is $NO_2$, by the following step (i-b):

(i-b) brominating the side-chain of 2-nitro-toluene compound VI to obtain the benzyl bromide II with X being $NO_2$.

In step (i-a1) the 2-nitro-toluene compound VI is converted to the corresponding methoxycarbamate compound VII. This conversion is preferably accomplished by the following sub-steps (i-a1') to (i-a1'''):

(i-a1') reducing a 2-nitro-toluene compound VI to the corresponding hydroxylamine compound of formula VIII,

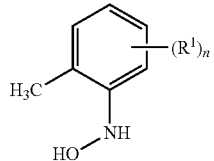
(VIII)

(i-a1") acylating the hydroxylamine VIII with a methyl haloformate to obtain a hydroxycarbamate compound of formula IX,

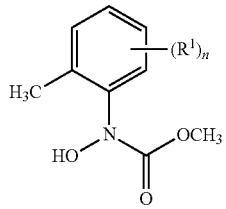
(IX)

(i-a1''') methylating the hydroxycarbamate compound IX to obtain the benzylamine compound IV'.

The variable n in the compounds of formulae VI, VII, VIII and IX is preferably 0, 1 or 2 and especially preferably 0 or 1. When n is 1, $R^1$ is preferably in the para or meta position to the attachment point of the nitro group, the radical $X^1$ or the derivatized amino group, respectively.

The radical $R^1$ in the compounds of formulae VI, VII, VIII and IX is preferably, if present, chlorine, bromine, $C_1$-$C_2$-alkyl, $C_1$-$C_2$-haloalkyl, $C_1$-$C_2$-alkoxy or $C_1$-$C_2$-haloalkoxy. $R^1$ is more preferably chlorine, $C_1$-$C_2$-alkyl or $C_1$-$C_2$-haloalkyl and even more preferably chlorine, methyl or halomethyl. Specifically, $R^1$ is 4-Cl, 3-Cl, 4-methyl, 3-methyl, 4-methoxy, 3-methoxy, 3-chloromethyl, 4-chloromethyl, 4-trifluoromethyl, 3-trifluoromethyl, 3-chloromethoxy, 4-chloromethoxy, 4-trifluoromethoxy, 3-trifluoromethoxy, 3,4-$Cl_2$, 3,4-dimethyl or 3,4-dimethoxy. The statements of position relate to the 1-position of the nitro group, the radical $X^1$ or the derivatized amino group, respectively, and the 6-position of the methyl substituent.

The conversions of steps (i-a1'), (i-a1") and (i-a1''') can be accomplished in analogy to the aforementioned steps (b-1), (b-2) and (b-3), respectively. The reactions and reaction conditions outlined herein for (b-1) to (b-3), including those identified as preferred, apply also to the corresponding steps (i-a1') to (i-a1''').

In addition to the heterogeneous hydrogenation described as preferred for step (b-1), the reduction in step (i-a1') is also preferably effected by reacting the 2-nitro-toluene compound VI with zinc/ammonium chloride, in analogy to a method described by S. Blechert, Liebigs Ann. Chem. 1985, 673.

In step (i-a2) compound VII is converted by free radical bromination using a suitable bromination reagent to obtain the benzylbromide II with X being a moiety $X^1$ as defined herein before.

Suitable bromination reagents here are those well known in the art for side-chain bromination of alkyl arenes, e.g. elemental bromine, N-bromosuccinimide (NBS) or a bromine source, such as hydrogen bromide, bromide salts or bromine, in the presence of an oxidation agent. In all cases the free radical bromination is usually initiated by irradiation with light or by employing an organic radical initiator, such as azobisisobutyronitrile (AIBN).

According to one embodiment of the invention for the conversion in step (i-a2) NBS is used as bromination reagent. The reaction is typically effected in an inert organic solvent, preferably selected from aromatic hydrocarbons and halogenated hydrocarbons.

In another embodiment of the invention the bromination in step (i-a2) is accomplished with a bromine source, in the presence of an oxidation agent according to EP 0336567 or EP 0999999, such as hydrogen peroxide. Hydrogen bromide is a preferred bromine source and hydrogen peroxide is preferably used as oxidation agent. The reaction can be initiated with light (cf. EP 0336567) or with an organic radical initiator (cf. EP 0999999).

The bromination of 2-nitro-toluene compound VI in step (i-b) can be accomplished in analogy to the aforementioned step (i-a2). The reactions and reaction conditions outlined herein for (i-a2), including those indentified as preferred, apply also to step (i-b).

In case the conversion in step (i-b) is carried out with NBS as bromination reagent the reaction is preferably initiated with an organic radical initiator, in particular AIBN, that is employed in a concentration of above 0.05 mol, more preferably from 0.1 to 0.3 mol-% and specifically from 0.15 to 0.25 mol-%, based in each case on 1 mol of on the 2-nitro-toluene compound VI.

The 2-chloromethyl-aniline compounds of formula I and the benzylamine compound of formula IV' are novel and are likewise part of the subject matter of the present invention:

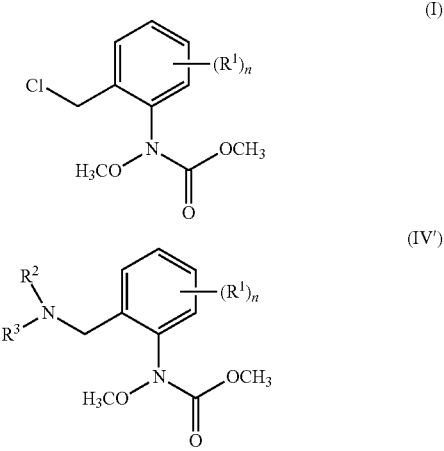

where n, $R^1$, $R^2$ and $R^3$ are each as defined above.

According to the above remarks, preference is given to those compounds of formula I in which n is 0.

Likewise, preference is given to compounds of formula IV' in which n is 0 and $R^2$ and $R^3$ are, independently of one another, selected from $C_1$-$C_3$-alkyl, $C_2$-$C_4$-alkoxyalkyl and $C_3$-$C_8$-cycloalkyl, or, together with the nitrogen atom to which they are bound, form a 5- or 6-membered ring that in addition to nitrogen may also contain a further heteroatom O or N. Particularly preferred are compounds of formula IV' in which n is 0 and $R^2$ and $R^3$ are both methyl, ethyl or propyl, or together with the nitrogen atom to which they are bound form a pyrrolidinyl moiety, a piperidinyl moiety or a morpholinyl moiety.

According to yet another aspect of the invention the 2-chloromethyl-aniline compounds of formula I are used for preparing 2-(pyrazol-3'-yloxymethylene)-anilide compounds of formula X,

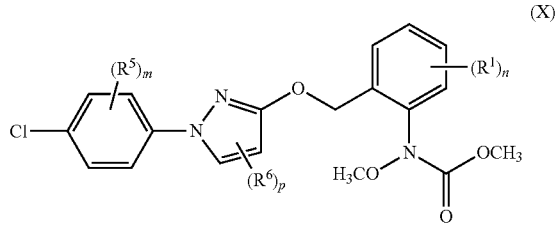

wherein the variables $R^1$ and n are as defined herein before,
m is 0, 1, 2 or 3,
p is 0, 1 or 2,
each $R^5$ is independently selected from halogen, $C_1$-$C_4$-alkyl, $C_1$-$C_4$-haloalkyl, $C_1$-$C_4$-alkoxy or $C_1$-$C_4$-haloalkoxy, and
each $R^6$ is independently selected from cyano, nitro, halogen, $C_1$-$C_4$-alkyl, $C_1$-$C_4$-alkoxy, $C_1$-$C_4$-haloalkoxy, $C_1$-$C_4$-alkylthio and $C_1$-$C_4$-alkoxycarbonyl.

According to the present invention, the process for preparing the compounds of formula X comprises the following steps:
(A) providing a 2-chloromethyl-aniline compound of formula I,

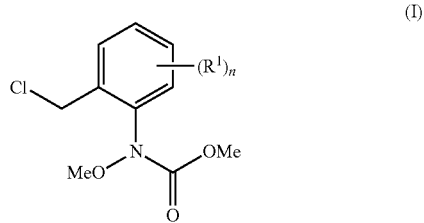

wherein n and $R^1$ are as defined herein before, by a process according to the process described above,
(B) reacting the 2-chloromethyl-aniline compound I with a phenylpyrazole compound of formula XI in the presence of a base,

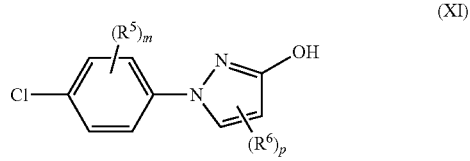

wherein the variables m, p, $R^5$ and $R^6$ are as defined for formula X,
to obtain the 2-(pyrazol-3'-yloxymethylene)-anilide compound of formula X.

The variable n in the compound of formula X is preferably 0, 1 or 2 and especially preferably 0 or 1. When n is 1, $R^1$ is preferably in the para or meta position to the attachment point of the radical $X^1$.

The radical $R^1$ in the compounds of formula X is preferably, if present, chlorine, bromine, $C_1$-$C_2$-alkyl, $C_1$-$C_2$-haloalkyl, $C_1$-$C_2$-alkoxy or $C_1$-$C_2$-haloalkoxy. $R^1$ is more preferably chlorine, $C_1$-$C_2$-alkyl or $C_1$-$C_2$-haloalkyl and even more preferably chlorine, methyl or halomethyl. Specifically, $R^1$ is 4-Cl, 3-Cl, 4-methyl, 3-methyl, 4-methoxy, 3-methoxy, 3-chloromethyl, 4-chloromethyl, 4-trifluoromethyl, 3-trifluoromethyl, 3-chloromethoxy, 4-chloromethoxy, 4-trifluoromethoxy, 3-trifluoromethoxy, 3,4-$Cl_2$, 3,4-dimethyl or 3,4-dimethoxy. The statements of position relate to the 1-position of the radical $X^1$ and the 6-position of the methylene substituent.

The variable m in the compounds of formulae X and XI is preferably 0 or 1 and especially preferably 0. When m is 1, $R^5$ is preferably in the meta position to the attachment point of the pyrazole moiety.

The radical $R^5$ in the compounds X and XI is preferably, if present, chlorine, fluorine, $C_1$-$C_2$-alkyl, $C_1$-$C_2$-haloalkyl, $C_1$-$C_2$-alkoxy or $C_1$-$C_2$-haloalkoxy. $R^5$ is more preferably, if present, chlorine, fluorine, $C_1$-$C_2$-alkyl or $C_1$-$C_2$-haloalkyl and even more preferably chlorine, methyl or halomethyl. Specifically, $R^5$ is 3-Cl, 3-methyl, 2-methyl, 3-methoxy, 3-chloromethyl, 3-trifluoromethyl, 3-chloromethoxy or 3-trifluoromethoxy. The statements of position relate to the 1-position of the pyrazole ring.

The variable p in the compounds X and XI is preferably 0 or 1 and especially preferably 0. When p is 1, $R^6$ is preferably attached to either the carbon atom in position 4 or in position 5 of the pyrazole ring.

The radical $R^6$ in the compounds of the formulae (X) and (XI) is preferably, if present, halogen, $C_1$-$C_2$-alkyl, $C_1$-$C_2$-haloalkyl, $C_1$-$C_2$-alkoxy, $C_1$-$C_2$-haloalkoxy or $C_1$-$C_2$-alkoxycarbonyl. $R^6$ is more preferably chlorine, fluorine, $C_1$-$C_2$-alkyl, $C_1$-$C_2$-haloalkyl or $C_1$-$C_2$-alkoxycarbonyl and even more preferably chlorine, fluorine, methyl, halomethyl or methoxycarbonyl.

In step (B) the preparation of the 2-(pyrazol-3'-yloxymethylene)-anilide compound X from the 2-chloromethyl-aniline compound I and the 1-phenyl-3-hydroxypyrazole compound XI is performed in a similar fashion as the etherification of a 2-nitro benzylhalide and a 3-hydroxypyrazole described in EP 0624155.

The conversion in step (B) is effected by reacting the compounds of formulae I and XI in the presence of an auxiliary base preferably in a solvent under appropriate reaction conditions.

Suitable solvents for dissolving or dispersing the reactants are preferably organic solvents that are inert toward the reactants. The choice of the solvent for the conversion in step (B) therefore depends on the particular reactants and reaction conditions selected in an individual case. In general, useful organic solvents here include those described herein before regarding the conversion of step (a).

Preferably the organic solvent for the conversion in step (B) is selected from halogenated aliphatic hydrocarbons, such as methylene chloride, aromatic hydrocarbons, such as chlorobenzene or toluene, alicyclic $C_3$-$C_6$-ethers, such as THF, amides such as DMF, DMA or NMP, DMSO, acetonitrile and mixtures thereof.

Suitable bases generally include those described herein before regarding the conversion of step (a) and are preferably selected from alkali metal carbonates, in particular sodium carbonate and potassium carbonate, alkali metal hydrogen carbonates, in particular sodium hydrogen carbonate and potassium hydrogen carbonate, alcoholates, in particular alkali metal alkoxides such as potassium tert-butoxide, and alkali metal hydroxides, in particular sodium hydroxide and potassium hydroxide, and specifically selected from sodium carbonate, potassium carbonate, potassium tert-butoxide and sodium hydroxide.

The base is in general used in an amount of from 0.8 to 3 mol, preferably 0.9 to 2.5 mol and in particular from 1 to 2 mol, based in each case on 1 mol of on the 2-chloromethyl-aniline compound I.

The reactants of formulae XI and I are generally employed in equimolar or nearly equimolar amounts. It may however be advantageous to use an excess of the 2-chloromethyl-aniline compound I, such as an 1 to 1.2 fold excess and in particular an 1.01 to 1.1 fold excess, in each case based on 1 mol of the 1-phenyl-3-hydroxypyrazole compound XI.

The etherification of step (B) is typically carried out at a temperature in the range from 0 to 100° C., preferably in the range from 5 to 80° C. and specifically in the range from 0 to 60° C.

The work-up of the reaction mixtures obtained by the conversion in step (B) and the isolation of the 2-(pyrazol-3'-yloxymethylene)-anilide compound X are effected in a customary manner. Preferably the reaction mixture from step (B) is worked up by dilution with an aqueous solution, in particular water, and then extracting the aqueous phase more than once with a suitable, essentially water-immiscible organic solvent, such as methyl tert-butyl ether. The combined organic phases are washed, e.g. with water and/or brine, dried and concentrated. The product thus isolated can be subjected to further purification steps known to a skilled person, such as for example crystallization, distillation or chromatography.

The 1-phenyl-3-hydroxypyrazole compounds XI required as starting substances in step (B) can be obtained by processes known in the art, for example those disclosed in WO 98/27062 and EP 0680954.

The 2-chloromethyl-anilines I of the present invention are readily accessible in good yield and high purity using processes of the invention that feature as direct precursors of compounds I the benzylamines IV' which are also compounds of the invention. In addition, according to further processes of the invention the 2-chloromethyl-anilines I can be coupled with the phenylpyrozoles XI to afford the 1-(pyrazol-3'-yloxymethylene)-anilides of formula X selectively and in high yield.

PREPARATION EXAMPLES

I. Preparation of the Benzylamine Compounds of the General Formula IV with the Variable X being $NO_2$ Example 1

N-(2-Nitrobenzyl)-pyrrolidine

To a solution of the crude 2-nitrobenzyl bromide (185 g, containing approximately 21% by weight of the 2-nitrobenzyl bromide (approximately 39 g, 180 mmol) besides the starting material 2-nitrotoluene and by-products of its bromination such as 2-nitrobenzal bromide) in chlorobenzene were added methylene chloride (500 ml) and pyrrolidine (28.1 g, 395 mmol). The solution was stirred at room temperature overnight. Then, the solution was cooled to 0° C. and aqueous solution of $H_2SO_4$ (200 g, 10% per weight) were added. The aqueous phase was extracted four times with methylene chloride (30 ml each). The aqueous phase was then treated with saturated aqueous solution of $K_2CO_3$ until the gas evolution had ceased. Then, it was extracted four times with methylene chloride (30 ml each). The combined organic phases were washed with water and brine and dried over $MgSO_4$ affording a yellow liquid (yield: 89%). The product obtained was sufficient pure (>95%) for subsequent steps without further purification.

$^1H$ NMR (500 MHz, $CDCl_3$): δ (ppm)=7.81 (dd, J=1.5 Hz, J=8.0 Hz, 1H); 7.67 (d, J=7.5 Hz, 1H); 7.53 (dt, J=1.0 Hz, J=7.5 Hz, 1H); 7.35 (dt, J=1.0 Hz, J=8.0 Hz, 1H); 3.91 (s, 2H); 2.47-2.51 (m, 4H); 1.72-1.76 (m, 4H).

$^{13}C$ NMR (125 MHz, $CDCl_3$): δ (ppm)=149.0; 134.8; 132.3; 130.5; 127.2; 123.9; 56.3; 53.9; 23.4.

The compounds of the following examples 2 to 5 were prepared in a manner analogous to the preparation of Example 1.

Example 2

Dimethyl-2-nitrobenzylamine

Crude nitrobenzyl bromide was reacted with dimethyl amine to afford a yellow liquid (yield: 97%, purity: >95%).

$^1H$ NMR (500 MHz, $CDCl_3$): δ (ppm)=7.81 (dd, J=1.0 Hz, J=8.0 Hz, 1H); 7.61 (d, J=7.5 Hz, 1H); 7.54 (dt, J=1.5 Hz, J=7.5 Hz, 1H); 7.38 (dt, J=1.5 Hz, J=8.0 Hz, 1H); 3.70 (s, 2H); 2.21 (s, 6H).

$^{13}C$ NMR (125 MHz, $CDCl_3$): δ (ppm)=149.6; 134.2; 132.3; 130.9; 127.7; 124.1; 60.1; 45.4.

Example 3

Diethyl-2-nitrobenzylamine

Crude nitrobenzyl bromide was reacted with diethyl amine to afford a yellow liquid (yield: 94%, purity: >95%).

$^1H$ NMR (500 MHz, $CDCl_3$): δ (ppm)=7.76 (dd, J=1.5 Hz, J=8.0 Hz, 1H); 7.70 (d, J=8.0 Hz, 1H); 7.51 (dt, J=1.0 Hz, J=7.5 Hz, 1H); 7.34 (dt, J=1.5 Hz, J=8.0 Hz, 1H); 3.83 (s, 2H); 2.47 (q, J=7.0 Hz, 4H); 0.97 (t, J=7.0 Hz, 6H).

$^{13}C$ NMR (125 MHz, $CDCl_3$): δ (ppm)=149.5; 135.6; 132.0; 130.6; 127.2; 123.8; 54.5; 46.9; 11.5.

Example 4

N-(2-Nitrobenzyl)-piperidine

Crude nitrobenzyl bromide was reacted with piperidine to afford a yellow liquid (yield: 83%, purity: >95%).

$^1H$ NMR (500 MHz, $CDCl_3$): δ (ppm)=7.77 (dd, J=1.5 Hz, J=8.0 Hz, 1H); 7.62 (d, J=7.5 Hz, 1H); 7.51 (dt, J=1.0 Hz, J=7.5 Hz, 1H); 7.35 (dt, J=1.0 Hz, J=8.0 Hz, 1H); 3.71 (s, 2H); 2.27-2.32 (m, 4H); 1.51 (pent., J=5.5 Hz, 4H); 1.37-1.42 (m, 2H).

$^{13}C$ NMR (125 MHz, $CDCl_3$): δ (ppm)=149.7; 134.4; 132.0; 130.7; 127.4; 123.9; 59.5; 54.4; 25.8; 24.1.

Example 5

N-(2-Nitrobenzyl)-morpholine

Crude nitrobenzyl bromide was reacted with morpholine to afford a yellow liquid (yield: 95%, purity: >95%).

$^1H$ NMR (500 MHz, $CDCl_3$): δ (ppm)=7.79 (dd, J=1.5 Hz, J=8.0 Hz, 1H); 7.59 (d, J=7.5 Hz, 1H); 7.54 (dt, J=1.5 Hz, J=7.5 Hz, 1H); 7.40 (dt, J=1.5 Hz, J=8.0 Hz, 1H); 3.77 (s, 2H); 3.63 (t, J=5.0 Hz, 4H); 2.41 (t, J=5.0 Hz, 4H).

$^{13}$C NMR (125 MHz, CDCl$_3$): δ (ppm)=149.6; 132.9; 132.0; 130.7; 127.7; 124.0; 66.5; 59.0; 53.2.

II. Preparation of Methoxycarbamate Compounds of the General Formula IV'

Example 6

N-Carbomethoxy-N-methoxy-(2-pyrrolidinomethyl)-aniline 6.1 N-hydroxy-(2-pyrrolidinomethyl)-aniline The N-(2-nitrobenzyl)-pyrrolidine (20 mmol) was dissolved in N-methyl-morpholine (20 ml). Platinum on carbon (5 mol-%, 0.17 mmol, 350 mg, Degussa Type F105 RS/W) was added. The reaction vessel was evacuated and flushed with nitrogen three times, before a hydrogen atmosphere was applied. Thin layer chromatography control showed complete consumption of the starting material after 4 hours. The platinum catalyst was removed by filtration over celite. The crude product was obtained after evaporation of all volatiles under reduced pressure in a purity of >90%, as measured by $^1$H NMR.

6.2 N-Carbomethoxy-N-hydroxy-(2-pyrrolidinomethyl)-aniline

The crude N-hydroxy-(2-pyrrolidinomethyl)-aniline was dissolved in methylene chloride (20 ml). A solution of NaHCO$_3$ (2.52 g, 30.0 mmol) in water (10 ml) was added. The biphasic mixture was cooled to 0° C.; at that point methyl chloroformate (1.70 g, 18.0 mmol) was added over 30 minutes. Stirring at 0° C. was continued for 60 minutes. The phases were separated and the aqueous phase was extracted three times with methylene chloride (50 ml each). The combined organic phases were dried over Na$_2$SO$_4$. The crude product was obtained after removal of all volatiles and subjected to flash column chromatography (on silica gel with cyclohexane/ethyl acetate) to give the pure hydroxycarbamate as a colorless liquid (yield: 44%).

$^1$H NMR (500 MHz, CDCl$_3$): δ (ppm)=7.28-7.44 (m, 4H); 3.80 (bs, 3H); 3.69 (s, 2H); 2.60 (bs, 4H); 1.79-1.83 (m, 4H).

$^{13}$C NMR (125 MHz, CDCl$_3$): δ (ppm)=156.2; 141.9; 135.8; 130.4; 129.4; 129.2; 128.6; 58.5; 53.4; 53.2; 23.3.

6.3 N-Carbomethoxy-N-methoxy-(2-pyrrolidinomethyl)-aniline

Sodium hydride (60% by weight in mineral oil, 84 mg, 2 mmol) was suspended in THF (5 ml). A solution of the N-carbomethoxy-N-hydroxy-(2-pyrrolidinomethyl)-aniline (2 mmol) in THF (5 ml) was added at 0° C. The resulting solution was stirred 60 minutes at 0° C. Then, methyl iodine (298 mg, 2.10 mmol) was added and the mixture was stirred at room temperature overnight. The mixture was diluted with methylene chloride and water; the aqueous phase was extracted three times with methylene chloride (10 ml each). The combined organic phases were washed with water and brine. The crude product was obtained after drying over MgSO$_4$ and evaporation of all volatiles. If necessary, the crude product can be purified by flash column chromatography (on silica gel with cyclohexane/ethylacetate) to give the pure methoxycarbamate as a colorless liquid (yield: 76%).

$^1$H NMR (500 MHz, CDCl$_3$): δ (ppm)=7.59 (d, J=8.0 Hz, 1H); 7.32-7.36 (m, 1H); 7.25-7.28 (m, 2H); 3.75 (s, 3H); 3.73 (s, 3H); 3.64 (s, 2H); 2.47-2.51 (m, 4H); 1.74-1.78 (m, 4H).

$^{13}$C NMR (125 MHz, CDCl$_3$): δ (ppm)=156.1; 138.4; 137.6; 129.9; 128.9; 128.0; 127.1; 61.8; 55.7; 54.3; 53.2; 23.7.

The compounds of the following examples 7 to 11 were prepared in a manner analogous to the preparation of Example 6.

Example 7

N-Carbomethoxy-N-methoxy-(2-dimethylaminomethyl)-aniline 7.1 N-Carbomethoxy-N-hydroxy-(2-dimethylaminomethyl)-aniline Dimethyl-2-nitrobenzylamine was reduced and subsequently reacted with methyl chloroformate by analogy to steps 6.1 and 6.2 to give a colorless liquid (yield: 11%).

$^1$H NMR (500 MHz, CDCl$_3$): δ (ppm)=7.36-7.42 (m, 2H); 7.28-7.32 (m, 2H); 3.80 (bs, 3H); 3.51 (s, 2H); 2.29 (s, 6H).

$^{13}$C NMR (125 MHz, CDCl$_3$): δ (ppm)=156.2; 142.1; 135.2; 131.1; 129.6; 129.3; 128.7; 62.3; 53.2; 44.4.

7.2 N-Carbomethoxy-N-methoxy-(2-dimethylaminomethyl)-aniline

N-Carbomethoxy-N-hydroxy-(2-dimethylaminomethyl)-aniline was methylated by analogy to step 6.3 to afford a colorless liquid (yield: 74%).

$^1$H NMR (500 MHz, CDCl$_3$): δ (ppm)=7.58 (d, J=9.5 Hz, 1H); 7.33-7.38 (m, 1H); 7.27-7.29 (m, 2H); 3.75 (s, 3H); 3.73 (s, 3H); 3.43 (s, 2H); 2.22 (s, 6H).

Example 8

N-Carbomethoxy-N-methoxy-(2-diethylaminomethyl)-aniline 8.1 N-Carbomethoxy-N-hydroxy-(2-diethylaminomethyl)-aniline Diethyl-2-nitrobenzylamine was reduced and subsequently reacted with methyl chloroformate by analogy to steps 6.1 and 6.2 to give a colorless liquid (yield: 11%).

$^1$H NMR (500 MHz, CDCl$_3$): δ (ppm)=7.40-7.44 (m, 1H); 7.38 (dt, J=2.0 Hz, J=6.5 Hz, 1H); 7.27-7.32 (m, 2H); 3.80 (bs, 3H); 3.62 (s, 2H); 2.58 (q, J=7.2 Hz, 4H); 1.10 (t, J=7.2 Hz, 6H).

$^{13}$C NMR (125 MHz, CDCl$_3$): δ (ppm)=155.9; 141.2; 135.3; 131.3; 129.2; 129.1; 128.4; 56.3; 52.9; 45.9; 10.4.

8.2 N-Carbomethoxy-N-methoxy-(2-diethylaminomethyl)-aniline

N-Carbomethoxy-N-hydroxy-(2-diethylaminomethyl)-aniline was methylated by analogy to step 6.3 to afford a colorless liquid (yield: 74%).

$^1$H NMR (500 MHz, CDCl$_3$): δ (ppm)=7.68 (d, J=7.5 Hz, 1H); 7.31-7.36 (m, 1H); 7.25-7.28 (m, 2H); 3.76 (s, 3H); 3.73 (s, 3H); 3.55 (s, 2H); 2.50 (q, J=7.0 Hz, 4H); 1.10 (t, J=7.0 Hz, 6H).

¹³C NMR (125 MHz, CDCl₃): δ (ppm)=155.8; 138.8; 137.6; 129.9; 128.7; 127.7; 126.8; 61.7; 53.2; 53.0; 47.1; 11.8.

Example 9

N-Carbomethoxy-N-methoxy-(2-piperidinomethyl)-aniline

9.1 N-Carbomethoxy-N-hydroxy-(2-piperidinomethyl)-aniline

N-(2-Nitrobenzyl)-piperidine was reduced and subsequently reacted with methyl chloroformate by analogy to steps 6.1 and 6.2 to give a colorless liquid (yield: 62%).
¹H NMR (500 MHz, CDCl₃): δ (ppm)=12.58 (bs, 1H); 7.34-7.44 (m, 2H); 7.26-7.30 (m, 2H); 3.80 (bs, 3H); 3.52 (s, 2H); 2.40-2.64 (m, 4H); 1.52-1.61 (m, 4H); 1.40-1.52 (m, 2H).
¹³C NMR (125 MHz, CDCl₃): δ (ppm)=155.9; 141.9; 134.5; 131.1; 129.0; 128.9; 128.2; 61.4; 53.5; 52.9; 25.1; 23.4.

9.2 N-Carbomethoxy-N-methoxy-(2-piperidinomethyl)-aniline

N-Carbomethoxy-N-hydroxy-(2-piperidinomethyl)-aniline was methylated by analogy to step 6.3 to afford a colorless liquid (yield: 66%).
¹H NMR (500 MHz, CDCl₃): δ (ppm)=7.58 (d, J=7.5 Hz, 1H); 7.30-7.35 (m, 1H); 7.25-7.28 (m, 2H); 3.76 (s, 3H); 3.73 (s, 3H); 3.45 (s, 2H); 2.35 (bs, 4H); 1.54 (pent., J=4.5 Hz, 4H); 1.40-1.45 (m, 2H).
¹³C NMR (125 MHz, CDCl₃): δ (ppm)=155.9; 138.0; 137.4; 130.1; 128.7; 127.9; 127.1; 61.7; 58.8; 54.0; 53.2; 26.0; 24.3.

Example 10

N-Carbomethoxy-N-methoxy-(2-morpholinomethyl)-aniline

10.1 N-Carbomethoxy-N-hydroxy-(2-morpholinomethyl)-aniline

N-(2-Nitrobenzyl)-morpholine was reduced and subsequently reacted with methyl chloroformate by analogy to steps 6.1 and 6.2 to give a colorless liquid (yield: 29%).
¹H NMR (500 MHz, CDCl₃): δ (ppm)=11.86 (bs, 1H); 7.39-7.45 (m, 2H); 7.31-7.34 (m, 2H); 3.80 (bs, 3H); 3.70 (bs, 4H); 3.59 (s, 2H); 2.55 (bs, 4H).
¹³C NMR (125 MHz, CDCl₃): δ (ppm)=155.9; 141.9; 133.7; 131.3; 129.6; 129.2; 128.6; 66.2; 61.2; 53.0; 52.8.

10.2 N-Carbomethoxy-N-methoxy-(2-morpholinomethyl)-aniline

N-Carbomethoxy-N-hydroxy-(2-morpholinomethyl)-aniline was methylated by analogy to step 6.3 to afford a colorless liquid (yield: 68%).
¹H NMR (500 MHz, CDCl₃): δ (ppm)=7.55 (d, J=8.0 Hz, 1H); 7.31-7.35 (m, 1H); 7.28-7.30 (m, 2H); 3.78 (s, 3H); 3.73 (s, 3H); 3.67 (t, J=4.5 Hz, 4H); 3.52 (s, 2H); 2.42 (t, J=4.5 Hz, 4H).
¹³C NMR (125 MHz, CDCl₃): δ (ppm)=155.9; 138.1; 136.1; 130.2; 128.7; 128.3; 127.4; 66.9; 61.8; 58.6; 53.7; 53.2.

III. Preparation of 2-chloromethyl-aniline Compounds of the General Formula I

Example 11

N-Carbomethoxy-N-methoxy-(2-chloromethyl)-aniline

N-Carbomethoxy-N-methoxy-(2-pyrrolidinomethyl)-aniline (0.5 mmol) was dissolved in acetonitrile (2 ml). To this solution was added isobutyl chloroformate (102 mg, 0.75 mmol) and the mixture was stirred at room temperature until HPLC control showed complete conversion (typically 4-16 hours). To the reaction mixture was added tert-butyl methyl ether (10 ml) and water (10 ml). The phase was extracted with tert-butyl methyl ether twice. The combined organic phases were washed with water and brine and dried over MgSO₄. The crude product could be used in the next step without further purification or subjected to flash column chromatography (on silica gel with cyclohexane/ethyl acetate) to deliver the pure benzyl chloride. After flash column chromatography a colorless liquid was obtained (yield: 94%)
¹H NMR (500 MHz, CDCl₃): δ (ppm)=7.51-7.55 (m, 1H); 7.34-7.39 (m, 3H); 4.64 (s, 2H); 3.79 (s, 3H); 3.76 (s, 3H).
¹³C NMR (125 MHz, CDCl₃): δ (ppm)=155.8; 137.9; 135.0; 130.5; 129.1; 129.0; 127.2; 62.3; 53.5; 41.8.

IV. Preparation of 2-(pyrazol-3'-yloxymethylene)-anilide Compounds of the General Formula X

Example 12

N-{2-[N'-(4-chloro-phenyl)-pyrazol-3'-oxymethyl]-phenyl}-N-methoxy-carbamic acid methyl ester N-Carbomethoxy-N-methoxy-(2-chloromethyl)-aniline (0.20 g, 0.87 mmol), 1-(4-chloro-phenyl)-3-hydroxypyrazole (0.17 g, 0.87 mmol) and K₂CO₃ were suspended in DMF (10 ml). The reaction mixture was stirred at 50° C. overnight. Thin layer chromatography control showed complete consumption of both starting materials. The suspension was diluted with tert-butyl methyl ether (100 ml), extracted four times with water and dried over MgSO₄. The crude product could be optionally purified by column chromatography on SiO₂ to give the desired product (0.25 g, 0.64 mmol, 74% yield). Alternatively, the product could be purified by recrystallization from ethanol/H₂O (3:1 (v/v)).

The invention claimed is:
1. Process for preparing a compound of formula (I),

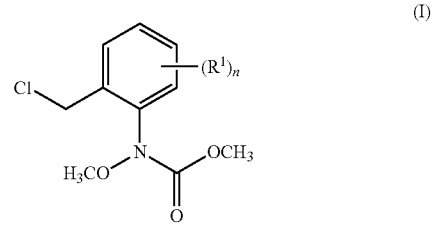

(I)

wherein:
n is 0, 1, 2 or 3,
each $R^1$ is independently selected from the group consisting of halogen, $C_1$-$C_4$-alkyl, $C_1$-$C_4$-haloalkyl, $C_1$-$C_4$-alkoxy and $C_1$-$C_4$-haloalkoxy, comprising:

(a) reacting a compound of formula (II) with a secondary amine of formula (III),

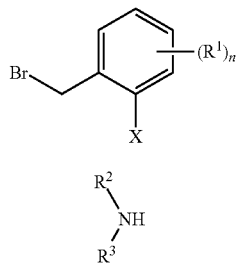
(II)

(III)

wherein:
n and $R^1$ are as defined for formula (I),
X is $NO_2$ or the moiety $X^1$, $$X^1: \quad \begin{array}{c} \text{OCH}_3 \\ | \\ -N \\ | \\ C=O \\ | \\ H_3CO \end{array}$$

$R^2$ and $R^3$ are each independently of the other selected from the group consisting of $C_1$-$C_6$-alkyl, $C_3$-$C_6$-alkenyl, $C_2$-$C_6$-alkoxyalkyl, $C_3$-$C_8$-cycloalkyl, phenyl and benzyl, wherein the phenyl moieties of the last two radicals mentioned may or may not carry 1, 2 or 3 substituents independently selected from halogen, $C_1$-$C_4$-alkyl and $C_1$-$C_4$-alkoxy, or
$R^2$ and $R^3$ together with the nitrogen atom to which they are bound form an unsubstituted or substituted 5-, 6- or 7-membered ring that in addition to nitrogen may also contain a further heteroatom O, S or N,
to obtain a compound of formula (IV),

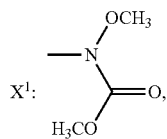
(IV)

wherein X, n, $R^1$, $R^2$ and $R^3$ are as defined herein before, (b) if appropriate, converting the compound of formula (IV), wherein X is $NO_2$, to a compound of formula (IV) in which X is the moiety $X^1$,
and (c) reacting the compound of formula (IV), wherein X is the moiety $X^1$, with an acyl chloride of formula (V),

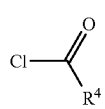
(V)

wherein:
$R^4$ is selected from the group consisting of $C_1$-$C_6$-alkoxy, $C_1$-$C_6$-haloalkoxy, $C_2$-$C_6$-alkenoxy, $C_2$-$C_6$-haloalkenoxy, $C_1$-$C_6$-alkyl, $C_1$-$C_6$-haloalkyl, $C_2$-$C_6$-alkenyl, $C_2$-$C_6$-haloalkenyl, benzyl, phenyl and benzoxy wherein the phenyl moieties of the last three radicals mentioned may or may not carry 1, 2 or 3 substituents independently selected from halogen, $C_1$-$C_4$-alkyl and $C_1$-$C_4$-alkoxy,
to obtain the compound of formula (I).

2. The process according to claim 1, wherein the variable n is 0.

3. The process according to claim 1, wherein the reaction according to step (a) is carried out in the presence of an auxiliary base.

4. The process of claim 1, wherein the secondary amine (III) is selected from the group consisting of dimethylamine, diethylamine, pyrrolidine, piperidine and morpholine.

5. The process of claim 1, wherein the conversion in step (b) is accomplished by the following sub-steps:
(b-1) reducing a benzylamine compound (IV), wherein X is $NO_2$, to obtain a hydroxylamine compound of formula (IVa),

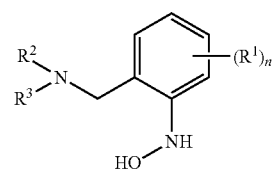
(IVa)

(b-2) acylating the hydroxylamine compound (IVa) with a methyl haloformate to obtain a hydroxycarbamate compound of formula (IVb),

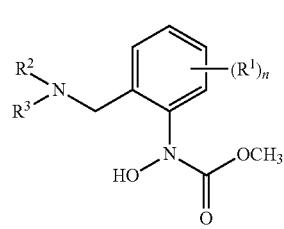
(IVb)

(b-3) methylating the hydroxycarbamate compound (IVb) to obtain the benzylamine compound (IV), wherein X is a moiety $X^1$.

6. The process of claim 1, where in step (c) a $C_1$-$C_6$-alkyl chloroformate is used as acyl chloride (V).

7. The process of claim 1, wherein the benzylbromide compound of formula (II) is provided by a method comprising the following steps:
(i) converting a 2-nitro-toluene compound of formula (VI),

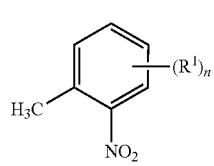
(VI)

to a benzylbromide compound of formula (II),

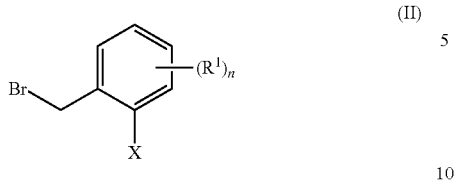
(II)

either, in case X is a moiety X¹, by the following sub-steps (i-a1) and (i-a2):

(i-a1) converting 2-nitro-toluene compound (VI) to a compound of formula (VII),

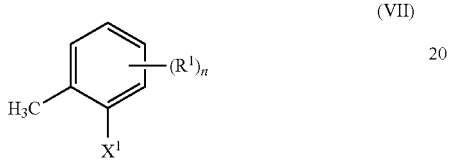
(VII)

(i-a2) brominating the side-chain of compound (VII) to obtain a benzylbromide (II) with X being a moiety X¹, or, in case X is $NO_2$, by the following step (i-b):

(i-b) brominating the side-chain of 2-nitro-toluene compound (VI) to obtain the benzylbromide (II) with X being $NO_2$.

8. The process according to claim 7, wherein the conversion in step (i-a1) is accomplished by the following sub-steps:

(i-a1') reducing a 2-nitro-toluene compound (VI) to the corresponding hydroxylamine compound of formula (VIII),

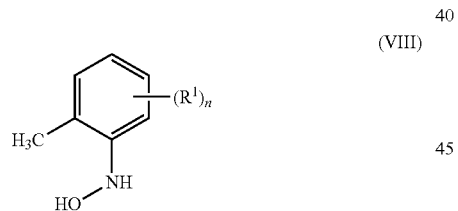
(VIII)

(i-a1") acylating the hydroxylamine (VIII) with a methyl haloformate to obtain a hydroxycarbamate compound of formula (IX),

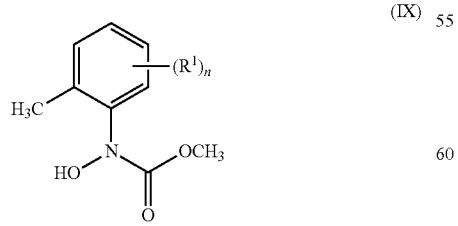
(IX)

(i-a1''') methylating the hydroxycarbamate compound (IX) to obtain the benzylamine compound (IV), wherein X is a moiety X¹.

9. The benzylamine compound of formula (IV'),

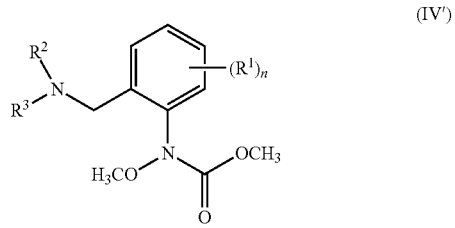
(IV')

wherein:

n is 0, 1, 2 or 3, and each $R^1$ is independently selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^2$ and $R^3$ are each independently of the other selected from the group consisting of $C_1$-$C_6$-alkyl, $C_3$-$C_6$-alkenyl, $C_2$-$C_6$-alkoxyalkyl, $C_3$-$C_8$-cycloalkyl and benzyl, wherein the phenyl moiety of benzyl may carry 1, 2 or 3 substituents independently selected from the group consisting of halogen, $C_1$-$C_4$-alkyl and $C_1$-$C_4$-alkoxy, or $R^2$ and $R^3$ together with the nitrogen atom to which they are bound form an unsubstituted or substituted 5-, 6- or 7-membered ring that in addition to nitrogen may also contain a further heteroatom O, S or N.

10. The benzylamine compound (IV') according to claim 9, wherein n is 0.

11. The benzylamine compound (IV') according to claim 9, wherein $R^2$ and $R^3$ are each ethyl or $R^2$ and $R^3$ together with the nitrogen atom to which they are bound form a pyrrolidinyl moiety, a piperidinyl moiety or a morpholinyl moiety.

12. Process for the preparation of a 2-(pyrazol-3'-yloxymethylene)-anilide compound of formula (X),

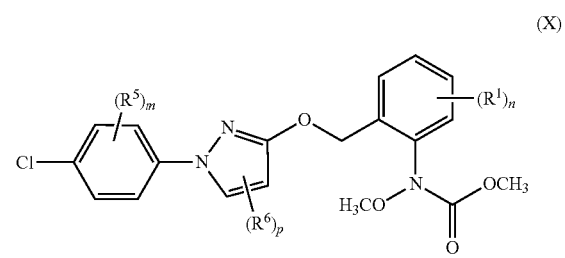
(X)

wherein n is 0, 1, 2 or 3, each $R^1$ is independently selected from the group consisting of halogen, $C_1$-$C_4$-alkyl, $C_1$-$C_4$-haloalkyl, $C_1$-$C_4$-alkoxy and $C_1$-$C_4$-haloalkoxy, m is 0, 1, 2 or 3, p is 0, 1 or 2, each $R^5$ is independently selected from halogen, $C_1$-$C_4$-alkyl, $C_1$-$C_4$-haloalkyl, $C_1$-$C_4$-alkoxy or $C_1$-$C_4$-haloalkoxy, and each $R^6$ is independently selected from cyano, nitro, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-alkoxycarbonyl, comprising:

(A) providing a 2-chloromethyl-aniline compound of formula (I),

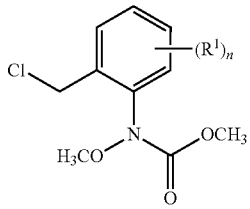

by the process according to claim 1, (B) reacting the 2-chloromethyl-aniline compound (I) with a phenylpyrozole compound of formula (XI) in the presence of a base,

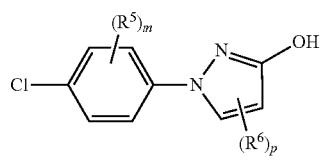

to obtain the 2-(pyrazol-3'-yloxymethylene)-anilide compound of formula (X).

13. The process according to claim 12, wherein each one of the variables n, m and p is 0.

14. The process according to claim 13, wherein said providing of the compound of formula (I) comprises (a) reacting a compound of formula (II) with a secondary amine of formula (III),

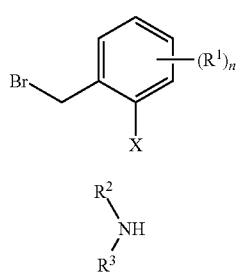

wherein:

n is 0, 1, 2 or 3, each $R^1$ is independently selected from the group consisting of halogen, $C_1$-$C_4$-alkyl, $C_1$-$C_4$-haloalkyl, $C_1$-$C_4$-alkoxy and $C_1$-$C_4$-haloalkoxy, X is $NO_2$ or the moiety $X^1$,

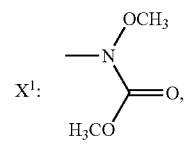

$R^2$ and $R^3$ are each independently of the other selected from the group consisting of $C_1$-$C_6$-alkyl, $C_3$-$C_6$-alkenyl, $C_2$-$C_6$-alkoxyalkyl, $C_3$-$C_8$-cycloalkyl, phenyl and benzyl, wherein the phenyl moieties of the last two radicals mentioned may or may not carry 1, 2 or 3 substituents independently selected from halogen, $C_1$-$C_4$-alkyl and $C_1$-$C_4$-alkoxy, or $R^2$ and $R^3$ together with the nitrogen atom to which they are bound form an unsubstituted or substituted 5-, 6- or 7-membered ring that in addition to nitrogen may also contain a further heteroatom O, S or N, to obtain a compound of formula (IV),

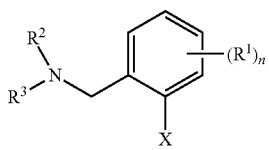

wherein X, n, $R^1$, $R^2$ and $R^3$ are as defined herein before, (b) if appropriate, converting the compound of formula (IV), wherein X is $NO_2$, to a compound of formula (IV) in which X is the moiety $X^1$, and (c) reacting the compound of formula (IV), wherein X is the moiety $X^1$, with an acyl chloride of formula (V),

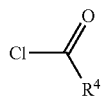

wherein:

$R^4$ is selected from the group consisting of $C_1$-$C_6$-alkoxy, $C_1$-$C_6$-haloalkoxy, $C_2$-$C_6$-alkenoxy, $C_2$-$C_6$-haloalkenoxy, $C_1$-$C_6$-alkyl, $C_1$-$C_6$-haloalkyl, $C_2$-$C_6$-alkenyl, $C_2$-$C_6$-haloalkenyl, benzyl, phenyl and benzoxy wherein the phenyl moieties of the last three radicals mentioned may or may not carry 1, 2 or 3 substituents independently selected from halogen, $C_1$-$C_4$-alkyl and $C_1$-$C_4$-alkoxy, to obtain the compound of formula (I).

15. The process according to claim 14, wherein the variable n is 0.

16. The process according to claim 14, wherein the reaction according to step (a) is carried out in the presence of an auxiliary base.

17. The process of claim 14, wherein the secondary amine (III) is selected from the group consisting of dimethylamine, diethylamine, pyrrolidine, piperidine and morpholine.

* * * * *